United States Patent [19]

Bierschenk et al.

[11] Patent Number: 5,523,496
[45] Date of Patent: Jun. 4, 1996

[54] FLUORINATION OF ACETALS, KETALS AND ORTHOESTERS

[75] Inventors: Thomas R. Bierschenk; Timothy J. Juhlke, both of Round Rock; Hajimu Kawa; Richard J. Lagow, both of Austin, all of Tex.

[73] Assignee: Exfluor Research Corporation, Austin, Tex.

[21] Appl. No.: 222,797

[22] Filed: Apr. 5, 1994

Related U.S. Application Data

[63] Continuation of Ser. No. 966,681, Oct. 26, 1992, Pat. No. 5,300,683, which is a continuation of Ser. No. 752,703, Aug. 30, 1991, Pat. No. 5,202,480, which is a continuation of Ser. No. 413,785, Sep. 28, 1989, Pat. No. 5,053,536, which is a continuation-in-part of Ser. No. 250,384, Sep. 28, 1988, abandoned.

[51] Int. Cl.⁶ ............................. C07C 43/30; C07C 43/11
[52] U.S. Cl. .......................... 568/603; 568/604; 568/615; 568/683; 568/684; 568/842
[58] Field of Search ....................... 568/603, 604, 568/615, 683, 684, 842

[56] References Cited

U.S. PATENT DOCUMENTS

| | | | |
|---|---|---|---|
| 3,721,696 | 3/1973 | Sianesi et al. | 260/463 |
| 3,847,978 | 11/1974 | Sianesi et al. | 260/535 H |
| 4,003,941 | 1/1977 | Crawford et al. | 260/463 |
| 4,113,435 | 9/1978 | Lagow et al. | 422/191 |
| 4,275,225 | 6/1981 | Krespan | 560/174 |
| 4,647,413 | 3/1987 | Savu | 260/544 |
| 4,755,330 | 7/1988 | Viola et al. | 260/544 |
| 4,755,567 | 7/1988 | Bierschenk et al. | 525/409 |
| 4,760,198 | 7/1988 | Bierschenk et al. | 568/615 |
| 4,827,042 | 5/1989 | Lagow et al. | 568/603 |
| 4,847,427 | 7/1989 | Nappa | 568/615 |
| 4,859,747 | 8/1989 | Bierschenk et al. | 525/409 |
| 5,053,536 | 10/1991 | Bierschenk et al. | 562/582 |
| 5,202,480 | 4/1993 | Bierschenk et al. | 562/582 |
| 5,300,683 | 4/1994 | Bierschenk et al. | 562/582 |
| 5,322,904 | 6/1994 | Bierschenk et al. | 525/331.6 |

FOREIGN PATENT DOCUMENTS

| | | |
|---|---|---|
| 640836 | 5/1962 | Canada. |
| 0077114 | 4/1983 | European Pat. Off.. |
| 54-119413 | 9/1979 | Japan. |
| 1192238 | 5/1970 | United Kingdom. |
| 89/10929 | 3/1989 | WIPO. |
| 90/03357 | 4/1990 | WIPO. |

OTHER PUBLICATIONS

Tacchi, et al., "Spectroscopic Studies on the Carboxylic Acids of Some Carbonyl Fluoride Telomers," *J. Mole. Struct.*, 14:293–302 (1972).

*Primary Examiner*—Porfirio Nazario-Gonzales
*Attorney, Agent, or Firm*—Hamilton, Brook, Smith & Reynolds

[57] ABSTRACT

Perfluoropolyethers and perhalogenated chlorofluoroether polymers are disclosed that can be prepared by fluorinating polymers made by the polymerization of acetals, ketals, polyacetals, polyketals and orthoesters with elemental fluorine.

20 Claims, No Drawings

FLUORINATION OF ACETALS, KETALS AND ORTHOESTERS

RELATED PATENT APPLICATIONS

This application is a continuation of U.S. patent application Ser. No. 07/966,681, filed Oct. 26, 1992, which issued as U.S. Pat No. 5,300,683 on Apr. 5, 1994, which is a continuation of U.S. patent application Ser. No. 07/752,703, filed Aug. 30, 1991, which issued as U.S. Pat. No. 5,202,480 on Apr. 13, 1993, which is a continuation of U.S. patent application Ser. No. 07/413,785, filed on Sep. 28, 1989, which issued as U.S. Pat. No. 5,053,536 on Oct. 1, 1991, which is a continuation-in-part of U.S. patent application Ser. No. 07/250,384, filed on Sep. 28, 1988, now abandoned, all of which are incorporated herein by reference.

BACKGROUND OF THE INVENTION

Perfluoropolyethers are highly regarded in the specialty lubricant field because of their wide liquid ranges, low vapor pressures and high thermal and oxidative stabilities. Because of these properties, (many of which are unique to fluorocarbons) they are excellent high performance lubricants, superior base stocks for greases, excellent lubricating oils, and heat transfer fluids. In addition, because of these uniquely outstanding properties, saturated perfluoropolyethers are of current interest as specialty sealants, elastomers and plastics.

In spite of their unlimited potential, only three perfluoropolyethers are commercially available to date because of the lack of fluorocarbon intermediates which are suitable for preparing the polymers. They are 1. DuPont's Krytox™ fluid which is made by polymerizing hexafluoropropylene oxide;
2. Demnum™ fluid, a product of Daikin, is obtained by ring opening polymerization of 2,2,3,3-tetrafluorooxetane using a catalyst with subsequent treatment of the highly fluorinated polyether with fluorine gas to give a perfluorinated product; and
3. Monticatini Edison's Fomblin Z™ and Fomblin Y™ fluids which are prepared by photooxidizing tetrafluoroethylene and hexafluoropropylene oxide, respectively, in the presence of oxygen.

A process has been described for preparing perfluoropolyethers by reaction of a hydrocarbon polyether with elemental fluorine in the presence of a hydrogen fluoride scavenger. See U.S. Pat. No. 4,755,567.

SUMMARY OF THE INVENTION

This invention relates to perfluorinated polyethers of the formula:

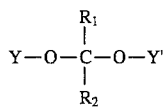

wherein Y and Y' are the same or different and are selected from the group consisting of perfluoroalkyl, perfluoroalkylether and perfluoroalkylpolyether wherein fluorine may be substituted with one or more halogen groups other than fluorine; wherein $R_1$ and $R_2$ are the same or different and are selected from the group consisting of —F, —Cl, —CF$_2$Cl, —CFCl$_2$, —CCl$_3$, perfluoroalkyl of one to ten carbons; wherein fluorine may be substituted with one or more halogen groups other than fluorine and wherein the perfluoroalkyl group may contain one or more ether oxygens. The perfluoroalkyl polyether which is Y and Y' may be atactic, isotactic or a block copolymer having 1 to 50 carbon atoms.

In another embodiment of the previous formula, when Y or Y' have 20 or fewer carbon atoms and $R_1$ is fluorine then $R_2$ is a group other than —CF$_3$ or —CF$_2$Cl.

This invention pertains to perfluorinated polyethers having the formula:

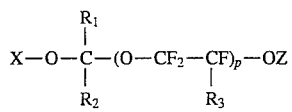

wherein $R_1$, $R_2$ and $R_3$ are the same or different and are selected from the group consisting of —F, —Cl, —CFTCl, —CFCl$_2$, —CCl$_3$, perfluoroalkyl of one to ten carbon atoms and perfluoroalkoxyalkyl of one to ten carbon atoms wherein one or more of the fluorine atoms may be substituted by a halogen atom other than fluorine; wherein X and Z are the same or different and are selected from the group consisting of —(CF$_2$)$_r$COF, —(CF$_2$)$_r$OCF$_3$, —(CF$_2$)$_r$COOH and —C$_r$F$_{2r+1-q}$Cl$_q$ wherein r is an integer from 1 to 12 and q is an integer from 0 to 25; p and t are the same or different and are integers from 1 to 50, provided that when p and t are one and $R_1$, $R_2$, $R_3$ and $R_4$ together are F, then $R_5$ or $R_6$ is a group other than fluorine. In a preferred embodiment, $R_1$, $R_2$ and $R_5$ are F, and p is an integer between 2 and 50.

This invention further relates to perfluorinated polyethers of the formula:

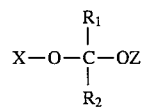

wherein X and Z are the same or different and are selected from the group consisting of —(CF$_2$)$_r$COF, —(CF$_2$)$_r$OCF$_3$, —(CF$_2$)$_r$COOH and —C$_r$F$_{2r+1-q}$Cl$_q$, wherein r is an integer from 1 to 12 and q is an integer from 0 to 25; wherein $R_1$ and $R_2$ are the same or different and are selected from the group consisting of —F, —Cl, —CF$_2$Cl, —CFCl$_2$, —CCl$_3$, perfluoroalkyl of one to ten carbon atoms and perfluoroalkoxyalkyl of one to ten carbon atoms wherein one or more of the fluorine atoms may be substituted by a halogen atom other than fluorine; and provided that $R_1$ and $R_2$ together are not F.

The perfluoropolyethers and the perhalogenated chlorofluoropolyethers of this invention can be used as lubricants, hydraulic fluids, thermal shock fluids, vapor phase soldering fluids and in numerous other applications in which an inert, nonflammable, oxidatively stable fluid is required. The low molecular weight perfluoropolyethers of the present invention have many useful applications in the electronics industry.

DETAILED DESCRIPTION OF THE INVENTION

This invention pertains to perfluorinated polyethers having the formula:

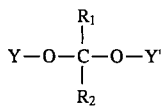

wherein Y and Y' are the same or different and are selected from the group consisting of perfluoroalkyl, perfluoroalkylether and perfluoropoxy(alkyleneoxy)alky; wherein fluorine may be substituted with one or more halogen groups other than fluorine; wherein $R_1$ and $R_2$ are the same or different and are selected from the group consisting of —F, —Cl, —$CF_2Cl$, —$CFCl_2$, —$CCl_3$ and perfluoroalkyl having 1 to 20 carbon atoms; and wherein the perfluoroalkyl group may contain one or more ether oxygens. The perfluoroalkylpolyether may be atactic, isotactic or a block copolymer having 1 to 50 carbon atoms. Examples of two polymers of this formula are Y—O—$CF_2$—OY and Y—O—CF—($CF_3$)—OY wherein Y is the same.

In another embodiment, this invention pertains to perfluorinated polyethers having the formula:

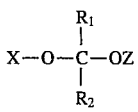

wherein X and Z are the same or different and are selected from the group consisting of —$(CF_2)_r$COF, —$(CF_2)_r$OCF_3$, —$(CF_2)_r$COOH and —$C_rF_{2r+1-q}Cl_q$, wherein r is an integer from 1 to 12 and q is an integer from 0 to 25; wherein $R_1$ and $R_2$ are the same or different and are selected from the group consisting of —F, —Cl, —$CF_2Cl$, —$CFCl_2$, —$CCl_3$, perfluoroalkyl of one to ten carbon atoms and perfluoroalkoxyalkyl of one to ten carbon atoms wherein one or more of the fluorine atoms may be substituted by a halogen atom other than fluorine; and provided that $R_1$ and $R_2$ together are not F.

This invention pertains to perfluorinated polyethers having the formula:

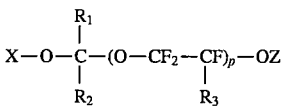

wherein $R_1$, $R_2$, and $R_3$ are the same or different and are selected from the group consisting of —F, —Cl, —$CF_2Cl$, —$CFCl_2$, —$CCl_3$, perfluoroalkyl of one to ten carbon atoms and perfluoroalkoxyalkyl of one to ten carbon atoms wherein one or more of the fluorine atoms may be substituted by a halogen atom other than fluorine; wherein X and Z are the same or different and are selected from the group consisting of —$(CF_2)_r$COF, —$(CF_2)_r$OCF_3$, —$(CF_2)_r$COOH and —$C_rF_{2r+1-q}Cl_q$ wherein r is an integer from 1 to 12 and q is an integer from 0 to 25; p and t are the same or different and are integers from 1 to 50, provided that when p and t are one and $R_1$, $R_2$, $R_3$ and $R_4$ together are F, then $R_5$ or $R_6$ is a group other than fluorine. In a preferred embodiment, $R_1$, $R_2$ and $R_5$ are F, and p is an integer between 2 and 50.

In another embodiment, this invention pertains to perfluorinated polyethers having the formula:

wherein Y and Y' are the same or different and are selected from the group consisting of perfluoroalkyl, perfluoroalkoxyalkyl and perfluoroalkyleneoxyalkyl; and wherein the polyether comprises fewer than 8 or greater than 12 or more carbon atoms provided that Y and Y' cannot both be —$CF_3$ or —$C_2F_5$. In a preferred embodiment, the polyether comprises from 12 to 20 carbon atoms.

In another embodiment, the invention includes perfluorinated polyethers having the formula:

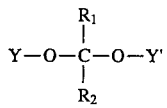

wherein Y and Y' are the same or different and are selected from the group consisting of perfluoroalkyl, perfluoroalkoxyalkyl and perfluoroalkyleneoxyalkyl; wherein $R_1$ and $R_2$ are the same or different and are selected from the group consisting of —Cl, —$CF_2Cl$, —$CFCl_2$, —$CCl_3$, perfluoroalkyl having 1 to 20 carbon atoms and perfluoroalkyleneoxyalkyl; and wherein the polyether comprises 12 or more carbon atoms. In a preferred embodiment, the polyether comprises 12 to 25 carbon atoms.

In another embodiment, the invention includes the perfluorinated polyethers having the formula:

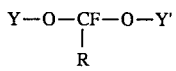

wherein Y and Y' are the same or different and are selected from the group consisting of perfluoroalkyl, perfluoroalkoxyalkyl and perfluoroalkyleneoxyalkyl; wherein R is selected from the group consisting of —Cl, —$CF_2Cl$, —$CFCl_2$, —$CCl_3$, perfluoroalkyl having 1 to 20 carbon atoms and perfluoroalkyleneoxyalkyl; and wherein the polyether comprises 12 or more carbon atoms. In a preferred embodiment, the polyether comprises 12 to 25 carbon atoms.

In another embodiment, the invention includes the perfluorinated polyethers having the formula:

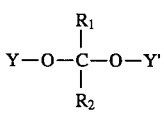

wherein Y and Y' are the same or different and are selected from the group consisting of perfluoroalkyl, perfluoroalkyleneoxyalkyl and perfluoropoly (alkyleneoxy) alkyl, wherein one or more of the fluorine atoms may be halogen atoms other than fluorine; wherein $R_1$ and $R_2$ are the same or different and are selected from the group consisting of —F, —Cl, —$CF_2Cl$, —CFCl, —$CCl_3$ and perfluoroalkyl having 1 to 20 carbon atoms wherein one or more of the fluorine atoms may be halogen atoms other than fluorine and wherein the perfluoroalkyl group may contain one or more ether oxygen atoms.

In another embodiment, the invention includes the perfluorinated polyethers having the formula:

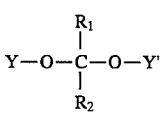

wherein Y and Y' are the same or different and are selected from the group consisting of perfluoroalkyl, perfluoroalkoxyalkyl and perfluoroalkyleneoxyalkyl, wherein $R_1$ and R are the same or different and are selected from the group consisting of —F, —Cl, —$CF_2Cl$, —$CFCl_2$, —$CCl_3$, perfluoroalkyl having 1 to 20 carbon atoms and perfluoroalkyleneoxyalkyl; and wherein the polyether contains at least one halogen atom other than fluorine.

This invention further pertains to a method of making perfluoropolyether and perhalogenated chlorofluoropolyether polymers.

The reaction of a diol with either an aldehyde, acetal, ketal or trialkyl orthoesters can be used to give a polyether if the starting materials and reaction conditions are carefully chosen. For example, if an aldehyde such as formaldehyde, acetaldehyde or butyraldehyde is reacted with a diol, a linear polyether can be made. Such a reaction is shown in Formula 1 below:

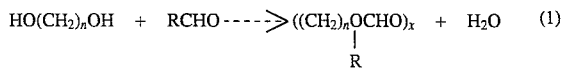

Suitable diols include ethylene glycol, diethylene glycol, triethylene glycol, tetraethylene glycol, other higher polyethylene glycols, propylene glycol, dipropylene glycol, tripropylene glycol, 2,2-dimethyl 1,3-propanediol, 1,4-butanediol, 1,5-pentanediol, 1,6-hexanediol, 1,7-heptanediol, 1,8-octanediol, 1,9-nonanediol, and 1,10-decanediol. Suitable aldehydes include formaldehyde, paraformaldehyde, 1,3,5-trioxane, acetaldehyde and its trimer, butyraldehyde and its trimer, pentanal, hexanal, 2-ethyl butanal, chloroacetaldehyde, dichloroacetaldehyde and trichloroacetaldehyde.

An alternative means of preparing the same polymer involves the reaction of an acetal with a diol. The synthesis involves the initial preparation of an acetal by reaction of an alcohol with the aldehyde as shown in Formula (2) below:

$$RCHO+2R'OH \rightarrow (R'O)_2C(R)H+H_2O \quad (2)$$

The acetal interchange is followed by a smoothly reversible reaction in acid media giving rise to the polyacetal. This reaction is given in Formula (3) below:

$$(R'O)_2C(R)H+HO(CH_2)_nOH \rightarrow HO((CH_2)_nOC(R)HO)_xH+2R'OH \quad (3)$$

Suitable acetals include the diethyl, dipropyl, dibutyl, dipentyl and diphenyl acetals of all of the previously mentioned aldehydes.

A well known reaction which is particularly well suited for preparing copolymers of acetaldehyde involves the reaction of divinyl ethers with diols. For example, ethylene glycol divinyl ether will react with ethylene glycol in the presence of H at −10° C. to give a 1:1 copolymer of ethylene glycol and acetaldehyde. Similarly, the divinyl ether of 1,5-pentanediol will react with 1,5-pentanediol to give a copolymer of pentanediol and acetaldehyde:

$$CH_2=CHOCH_2CH_2CH_2CH_2CH_2OCH=CH_2 + \quad (4)$$

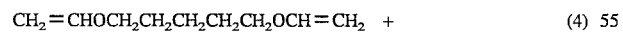

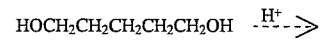

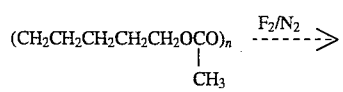

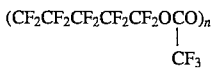

Terpolymers can be prepared by reacting a divinyl ether of one diol with a diol of a different structure. For example, the divinyl ether of ethylene glycol will react with 1,3-propanediol to yield a polyether after fluorination having the following structure:

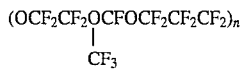

The divinyl ethers are conveniently formed by reacting a dihydroxyl terminated compound with acetylene at 160° C. in the presence of KOH.

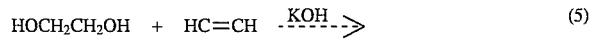

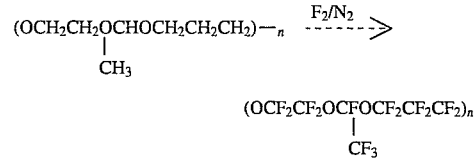

A variety of aldehydes can be polymerized and fluorinated to give perfluoropolyethers that have unique and often useful properties. For example, chloroacetaldehyde can be polymerized and fluorinated to give perfluoropolychloroacetaldehyde. Similarly, dichloroacetaldehyde and trichloroacetaldehyde can be polymerized and fluorinated to give the perfluorocarbon analogue of the polyethers. Chlorofluoroethers such as these are potentially useful nonflammable aircraft hydraulic fluids. Their relatively high oxidative stability and low compressibility make them attractive candidates. Other aldehydes such as acetaldehyde, trifluoroacetaldehyde and propanal can be polymerized and fluorinated to give stable polymers.

Ketals undergo a facile reversible metathesis reaction with alcohols to give polyketals as shown below in Formula (4):

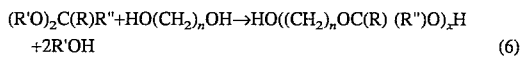

The list of useful ketals would include
2,2-dimethoxypropane, 2,2-dimethoxybutane,
2,2-dimethoxypentane, 2,2-dimethoxyhexane,
3,3-dimethoxypentane, 3,3-dimethoxyhexane as well as the diethoxy, dipropoxy, dibutoxy and diphenoxy analogues of the previously mentioned ketals.

The direct reaction of a ketone with an alcohol, a reaction analogous to the reaction of an aldehyde with an alcohol, generally works for several isolated ketones. For this reason, the ketal is normally used.

The reaction of a trialkyl or triaryl orthoester with alcohols gives formats according to the reaction presented in Formula (5):

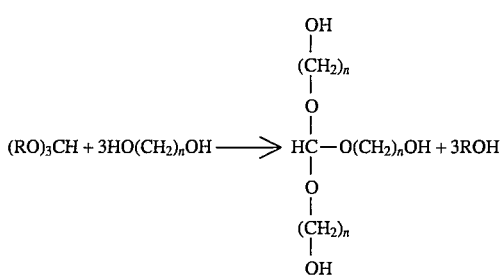

$$(RO)_3CH + 3HO(CH_2)_nOH \longrightarrow HC\begin{matrix}O\\|\\-O(CH_2)_nOH\\|\\O\end{matrix} + 3ROH \quad (7)$$

Useful orthoesters include trimethylorthoformate, triethylorthoformate, tripropylorthoformate, tributylorthoformate, triphenylorthoformate, trimethylorthoacetate, triethylorthoacetate, tripropylorthoacetate, tributylorthoacetate, triphenylorthoacetate, trimethylorthopropionate, triethylorthopropionate, tripropylorthopropionate, tributylorthopropionate, triphenylorthopropionate, trimethylorthobutyrate, triethylorthobutyrate, tripropylorthobutyrate, tributylorthobutyrate and triphenylorthobutyrate.

It should be clear from the proceeding discussions that a wide variety of linear as well as highly branched polyethers can be made using these interchange reactions. By carefully choosing the appropriate diol and aldehyde it is possible to prepare cyclic acetals which can often be polymerized to give polyethers. For example, formaldehyde reacts with diethylene glycol to give 1,3,6-trioxocane which can be polymerized to give linear polyacetals as shown in Formula (6) below:

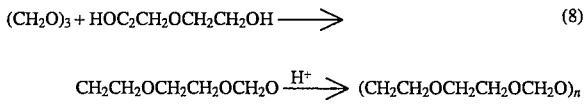

$$(CH_2O)_3 + HOC_2H_2OCH_2CH_2OH \longrightarrow \quad (8)$$

$$CH_2CH_2OCH_2CH_2OCH_2O \xrightarrow{H^+} (CH_2CH_2OCH_2CH_2OCH_2O)_n$$

Similarly, the cyclic products formed by the reaction of trimethylene glycol with dibutyl formal and the reaction of hexamethylene glycol with propionaldehyde polymerize in the presence of an acid to given linear polymers as described in U.S. Pat. No. 2,071,252. In general, if the glycol is 1,4-butanediol or higher a linear polymer is formed whereas glycols having fewer carbons generally form rings. If the glycol used is a polyether glycol, such as diethylene glycol or triethylene glycol, the linear polymer represents a thermodynamically more stable structure. However, it is often possible to convert the linear polyether to the cyclic ether by vacuum pyrolysis.

Up to this point the discussion has been limited to relatively high molecular weight materials prepared from diols. If the same reactions are carried out using monohydridic alcohols a single compound is made which typically has a much lower molecular weight having essentially the formula shown after fluorination

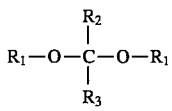

wherein $R_1$, $R_2$ and $R_3$ are the same or different and are selected from the group consisting of —F, perfluoroalkyl of one to ten carbon atoms, which may contain ether oxygens and wherein fluorine may be optionally substituted with one or more halogen groups other than fluorine.

For example, a monohydridic alcohol will react with an aldehyde, acetal or divinyl ether to give a new acetal.

$$2ROH + HCR'O \rightarrow RO\text{—}CHR'\text{—}OR \quad (9)$$

$$2ROH + (R''O)_2CR'H \rightarrow RO\text{—}CHR'\text{—}OR \quad (10)$$

$$2ROH + CH_2=CHOR'OCH=CH_2 \rightarrow ROCH(CH_3)OR'OCH(CH_3)OR \quad (11)$$

The reaction of an alcohol with a ketal will result in an interchange reaction given rise to a ketal.

$$2ROH + (R''O)2CR'R''' \rightarrow RO\text{—}CR'R'''\text{—}OR \quad (12)$$

A monohydridic alcohol will react with an orthoester to give another orthoester.

$$3ROH + (R'O)_3CH \rightarrow (RO)_3CH \quad (13)$$

Low molecular weight unimolecular polyethers can be made by reacting any of the previously mentioned aldehydes, acetals, ketals or orthoesters with a monohydridic alcohol such as methoxyethanol, ethoxyethanol, butoxyethanol, diethylene glycol methyl ether, diethylene glycol ethyl ether, diethylene glycol butyl ether, triethylene glycol methyl ether, triethylene glycol ethyl ether, triethylene glycol butyl ether, tetraethylene glycol methyl ether, tetraethylene glycol ethyl ether, tetraethylene glycol butyl ether, pentaethylene glycol methyl ether, pentaethylene glycol ethyl ether, pentaethylene glycol butyl ether, propylene glycol methyl ether, propylene glycol ethyl ether, propylene glycol butyl ether, dipropylene glycol methyl ether, dipropylene glycol ethyl ether, dipropylene glycol butyl ether, tripropylene glycol methyl ether, tripropylene glycol ethyl ether and tripropylene glycol butyl ether.

Low molecular weight, unimolecular perfluoropolyether fluids find numerous application in the electronics industry. Fluorocarbon fluids are useful as coolants and insulators in high-voltage electronic equipment, as immersion medium for leak testing, as heat transfer agents for vapor phase soldering, as fluids for direct cooling of electronic devices and as thermal shock fluids. Fluorinated polyether acetals, such as the ones described herein may also find uses as fluorocarbon blood substitutes.

Conversion of the hydrocarbon polyether to a perfluoropolyether can be accomplished by reacting the polyether with elemental fluorine. Because of the reactive nature of elemental fluorine, it is preferred to dilute the fluorine with an inert gas such as nitrogen or helium. Typically, the fluorine is diluted with nitrogen and as higher degrees of fluorination are achieved, the concentration of fluorine is usually increased. Due to the extreme exothermicity of the reaction, the fluorination must be carried out slowly unless provisions have been made for rapidly removing the heat of reaction. Submersion of the reactor in a cooled liquid bath is usually adequate for achieving commercially acceptable rates of reaction.

Fluorine gas is the preferred fluorinating agent and is commercially available at sufficiently high purity levels and at an acceptable cost. The fluorination reaction is generally carried out at a temperature between −80° and +150° C., preferably between −10° and +40° C. It can be carried out in a reactor containing an ultraviolet radiation source or in the dark. Using the preferred temperature range, it is not necessary to have an ultraviolet light source since the fluorine is sufficiently reactive. If an ultraviolet light source is used, however, a wavelength between 250 and 350 nm is preferred. When the reactor is irradiated with an external light source, a transparent window is needed which does not react with either fluorine or hydrogen fluoride. A quartz lens coated with a thin film of fluorinated ethylene-propylene copolymer works well.

The fluorination reaction can be carried out in a variety of ways. The polyether can be coated on sodium fluoride powder to give a free-flowing powder which can be fluorinated in either a stationary tube, in a rotating drum—type reactor, or in a fluidized bed. See U.S. Pat. 4,755,567.

Alternatively, the polyether, if soluble, can be dissolved in a solvent inert to fluorine and can be fluorinated while in solution using a liquid phase fluorination reactor. See U.S. patent application Ser. No. 07/250,376, entitled "Liquid Phase Fluorination", by Thomas R. Bierschenk, Timothy J. Juhlke, Hajimu Kawa and Richard J. Lagow, filed Sep. 28, 1988, now abandoned, and U.S. Pat. No. 5,093,432, which is a continuation-in-part of 07/250,376, issued to Bierschenk et al. (Mar. 3, 1992), the teachings of which are incorporated by reference herein. A typical laboratory-size reactor for example, has a volume of about 10 liters and contains approximately 2 to 8 liters of a suitable solvent. Perhalogenated chlorofluorocarbons are used as the solvent. 1,1,2-trichlorotrifluoroethane works well since it does not react appreciably with fluorine when the preferred temperature range is used.

The reaction can be carried out either in a batch mode where all of the polyether is dissolved in a solvent prior to fluorination or in a continuous mode where the polyether is continuously being pumped into the solvent as fluorine is being bubbled through the solution. Generally speaking, the continuous operation gives a preferred yield, better product quality and improved rates.

If the polyether is insoluble in the liquid fluorination medium, it can still be fluorinated in high yield as an emulsion in the liquid phase reactor. An emulsified solution of the polyether and the fluorineinert liquid fluorination medium can either be pumped into the reactor or the reactant can be emulsified in the reactor with the fluorination medium prior to the reaction.

An alternative method for fluorinating polyethers which are insoluble in the liquid fluorination medium involves adding a solvent to the polyether which allows limited solubility of polyether in the liquid fluorination medium. For clarity, 1,1,2-trichlorotrifluoroethane has been selected as the liquid fluorination medium; however, other highly fluorinated solvents can also be used. Typically, a mixture containing one part polyether, one part solvent and one part 1,1,2-trichlorotrifluoroethane will give a homogeneous solution. A solvent is selected which readily dissolves the polyether. Often it is possible to choose a solvent which will consume little, if any, of the fluorine gas. Trifluoroacetic anhydride, trifluoroacetic acid, chloroform, 1,1,2-trichloroethylene and 1,1,2-trichloroethane work especially well.

The polyether/solvent/1,1,2-trichlorotrifluoroethane solution is metered into a vigorously stirred fluorination reactor. As the polyether solution contacts the 1,1,2-trichlorotrifluoroethane in the reactor, an emulsion is formed. The polyether droplets in the solution are in most cases sufficiently small that they react quickly with the fluorine gas with negligible side reactions.

When carrying out the reaction in a liquid fluorination medium, a hydrogen fluoride scavenger such as sodium fluoride or potassium fluoride may or may not be present in the solution to scavenge the by-product hydrogen fluoride. However, the preferred mode for carrying out the reaction is with a sufficient quantity of sodium fluoride being present to complex with all of the hydrogen fluoride formed. When fluorinating ethers in the presence of sodium fluoride, improved yields are obtained while chain cleavage and rearrangements are minimized. See U.S. Pat. No. 4,755,567, the teachings of which are incorporated herein by reference.

Products produced using the methods just described usually have a residual hydrogen content of 0.001% or less. In order to obtain a fluid which is essentially free of residual hydrogen and void of any reactive terminal groups such as acyl fluoride groups resulting from chain degradation reactions, a final fluorination near 175° C. with 30% fluorine for several hours works well.

The following examples will further illustrate the invention, but are not to be construed as limiting its scope.

EXAMPLE 1

400 g butoxyethoxyethanol (2.5 mol), 48 g paraformaldehyde (1.6 mol), 300 ml benzene and 5 g ion exchange resin (acid form) were placed in a 1 liter stirred flask. A water separator attached to a reflux condenser was used to collect the water produced as the alcohol and aldehyde reacted. After approximately 6 hours, the reaction was complete and the solution was filtered to remove the resin. Vacuum distillation of the solution to 120° C. gave 414 g of a product (99% yield) which was essentially free of benzene and unreacted starting materials.

The hydrocarbon product was fluorinated in a 22 liter stirred tank reactor which contained 6 liters of 1,1,2-trichlorotrifluoroethane and 1300 g sodium fluoride powder. A gas dispersion tube in the bottom of the reactor provided an inlet for the fluorine and nitrogen gasses. 275 grams of the hydrocarbon reactant was diluted with 1,1,2-trichlorotrifluoroethane, in a separate vessel, to give a total volume of 700 ml. This solution was metered into the fluorination reactor over a 20 hour period. The reactor temperature was maintained at 0° C. with external cooling throughout the reaction while the fluorine flow was set at a level 10% higher than that required to theoretically replace all of the hydrogens on the material entering the reactor. Upon completion of the reaction, the fluorine was turned off, the reactor was removed from the low temperature bath and purged for 30 min with nitrogen (2 liters/min) to remove the unreacted fluorine.

Filtration of the reaction product followed by distillation to remove the 1,1,2-trichlorotrifluoroethane gave 642 g of a highly fluorinated fluid (80% yield). Treatment of the fluid at 260° C. with 30% fluorine for several hours gave a perfluorinated fluid having essentially the following structure:

$CF_3CF_2CF_2CF_2OCF_2CF_2OCF_2CF_2OCF2OCF_2CF_3$.

The elemental analysis was consistent with the formula: $C_{17}F_{36}O_6$ b.p. 226.5° C. $^{19}F$ NMR ($\delta$ppm vs $CFC_3$) −89.0, −90.7: $CF_2CF_2O$; −51.8: $CF_2O$; −81.8, −83.7, −126.7: $CF_3CF_2CF_2CF_2O$.

EXAMPLE 2

A mixture of 400 g triethylene glycol monoethyl ether (2.2 mol), 48 g paraformaldehyde (1.6 mol), 150 ml toluene and 10 g of an acid ion exchange resin was refluxed for 6 hours in a 1 liter flask equipped with a water separator and reflux condenser. Filtration of the product followed by distillation gave a quantitative yield of the desired product.

Fluorination of 201 g of the material in a stirred liquid fluorination reactor containing 6 liters of 1,1,2-trichlorotrifluoroethane and 1055 g sodium fluoride gave 401 g fluid in an 18 hour reaction at 0° C. Distillation of the crude product mixture gave 355 g of the perfluorinated fluid: 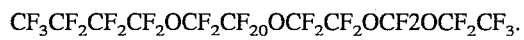
$CF_3CF_2OCF_2CF_2OCF_2CF_2OCF_2CF_2OCF_2OCF_2CF_2OCF_2-CF_2OCF_2CF_3$ The elemental analysis was consistent with the formula: $C_{17}O_8F_{36}$ b.p. 217° C.

$^{19}$F NMR (ppm vs CFCl$_3$): −51−7:CF$_2$O; −87.3, −90.7:CF$_2$CF$_2$; −88.7 CF$_2$CF$_2$O.

EXAMPLE 3

Into a 1 liter flask were placed 600 g triethylene glycol butyl ether (2.91 mol), 74 g paraformaldehyde (2.46 mol), 150 ml benzene and 10 g of an acidic ion exchange resin. The mixture was refluxed for 5 hours as water was removed as the water/benzene azeotrope. Filtration of the product and removal of the benzene by distillation gave a 90% yield of the polyether. 259 grams of the product were diluted with 400 ml 1,1,2-trichlorotrifluoroethane and were slowly metered into a 10° C. reactor containing 5.7 liters of 1,1,2-trichlorotrifluoroethane and 1200 g sodium fluoride powder. A fluorocarbon fluid (660 g, 88.7% yield) was obtained following filtration and removal of the 1,1,2-trichlorotrifluoroethane. Fluorination of the fluid at 220° C. with 30% fluorine for 12 hours followed by distillation gave the following fluid in 60% yield: CF$_3$CF$_2$CF$_2$CF$_2$OCF$_2$CF$_2$OCF$_2$CF$_2$OCF$_2$CF$_2$OCF$_2$OCF-CF$_2$OCF$_2$CF$_2$OCF$_2$CF$_2$OCFCF$_2$CFCF$_3$ b.p. 262° C.

$^{19}$F NMR (δppm vs CFCl$_3$): −88.7, −90.5:CF$_2$CF$_2$O; 51.7:CF$_2$O; −81.6, −83.4, −126.5:CF$_3$CF$_2$CF$_2$CF$_2$O.

EXAMPLE 4

Into a stirred 1 liter flask equipped with a water separator were charged 350 g tetraethylene glycol butyl ether (1.40 mol), 35 g paraformaldehyde (1.18 mol), 200 ml benzene and 10 g ion exchange resin. The mixture was refluxed until the water production ceased. Filtration of the product followed by removal of the lights via a vacuum distillation to 140° C. gave 343 g of a light yellow fluid.

A 306 g sample of the fluid was diluted with 450 ml of 1,1,2-trichlorotrifluoroethane and slowly pumped into a −6° C. reactor over a 23 hour period. The reactor contained 1450 g of sodium fluoride powder to react with the hydrogen fluoride formed during the reaction along with 6 liters of 1,1,2-trichlorotrifluoroethane. Filtration of the product followed by distillation gave 736 g of fluid.

Treatment of the fluid at 250° C. with 30% fluorine gave a clear, odorless fluid which upon distillation gave a 52% yield of a material having the following structure:

CF$_3$CF$_2$CF$_2$CF$_2$OCF$_2$CF2OCF$_2$CF$_2$OCF$_2$CF$_2$OCF$_2$CF$_2$-OCF$_2$OCF$_2$CF$_2$OCF$_2$OCF$_2$CF$_2$OCF$_2$CF$_2$CF$_2$CF$_3$
b.p. 296.7° C.

$^{19}$F NMR (δppm vs CFCl$_3$): −51.8:CF$_2$O; −88.8, −90.6:CF$_2$CF$_2$O; −81.7, −83.6, −126.7:CF$_3$CF$_2$CF$_2$CF$_2$O.

EXAMPLE 5

Dipropylene glycol methyl ether (300 g, 2.04 mol), 0.8 g paraformaldehyde (2.03 mol), 100 ml toluene and 5 g of an acid catalyst were mixed in a stirred 1 liter flask. After refluxing for 12 hours, the solution was filtered and distilled to give 203 g of a fluid which boiled at 140° C. at 0.05 mm Hg. The fluid (200 g) was mixed with 300 ml 1,1,2-trichlorotrifluoroethane and 950 g sodium fluoride powder. The reaction was complete in 18 hours after which time the solution was filtered and distilled to give 405 g of a clear liquid having the following structure (71% yield):

CF$_3$OC$_3$F$_6$OC$_3$F$_6$OCF$_2$OC$_3$F$_6$OC$_3$F$_6$OCF$_3$
The fluid contains CF(CF$_3$)CF$_2$OCF(CF$_3$)CF$_2$O, CF(CF$_3$)CF$_2$OCF$_2$CF(CF$_3$)O and CF$_2$CF(CF$_3$)OCF(CF$_2$)CF$_2$O linkages. The structure was confirmed by F NMR and elemental analysis:

$^{19}$F NMR (δppm vs CFCl$_3$):−47.6:CF$_3$O; −54.0:CF$_2$O; −80. 0: CF(CF$_3$) CF$_2$O; −82 to −87 :CF(CF$_3$) CF$_2$O; −140 to −150: CF (CF$_3$) CF$_2$O.

EXAMPLE 6

A mixture of 300 g tripropylene glycol methyl ether (6.46 mol), 33.7 g paraformaldehyde (1.12 mol), 150 ml benzene and 3 g ion exchange resin was refluxed for 6 hours in a 1 liter flask equipped with a water separator and reflux condenser. Filtration of the product followed by vacuum distillation of the lights gave 166 g of a product with a boiling point above 150° C. at 0.05 mm Hg.

Fluorination of 145 g of the material, dissolved in 450 ml of 1,1,2-trichlorotrifluoroethane, in a stirred fluorination reactor containing 6 liters of 1,1,2-trichlorotrifluoroethane and 700 g of sodium fluoride gave 244 g of a fluorocarbon product in a 20 hour reaction at −3° C. Distillation of the product gave 180 g of the perfluorinated fluid:

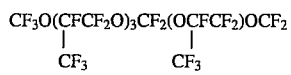

where the hexafluoropropylene oxide units are attached randomly in a head to head, head to tail and tail to tail fashion.

b.p. 260.0° C.

$^{19}$F NMR (δppm vs CFCl$_3$):−47.3, −56.0:CF$_3$O; −54.0:CF$_2$O; −80.0 CF(CF$_3$)CF$_2$O; −83.0 −85.3:CF(CF$_3$)CF$_2$O; −145.3, −146.0:CF(CF$_3$)CF$_2$O.

EXAMPLE 7

A mixture of 600 g diethylene glycol and 30 g potassium hydroxide was heated to 160° C. in a 1 liter flask. Acetylene gas was bubbled through the solution as it was rapidly stirred. The reaction was stopped after 48 hours and the product was extracted with water several times to remove any unreacted diethylene glycol. The product, a divinyl ether of diethylene glycol, was recovered by distillation (b.p. 196° C.) in about an 80% yield.

A 1 liter flask cooled to −10° C. was charged with 250 g triethylene glycol ethyl ether and a catalytic amount of methane sulfonic acid. To this solution was added slowly 100 g diethylene divinyl ether. Following the addition, the flask was slowly warmed to room temperature over a 3 hour period. The product was distilled to 150° C. at 0.05 mm Hg to remove any unreacted starting materials.

The product from the above reaction can be fluorinated at 20° C. using the procedures outlined in the previous liquid phase fluorination examples to give a perfluorinated fluid of the following structure: CF$_3$CF$_2$O (CF$_2$CF$_2$O)$_3$CF (CF$_3$)O(CF$_2$CF$_2$O)$_3$CF(CF$_3$)O(CF$_2$CF$_2$O)$_3$CF$_2$CF$_3$C$_{24}$F$_5$O$_{11}$
b.p. 300° C.

EXAMPLE 8

A mixture of 600 g 1,5-pentanediol and 30 g potassium hydroxide was heated to 160° C. in a 1 liter flask. Acetylene gas was bubbled through the solution as it was rapidly stirred. The reaction was stopped after 40 hours and the product was washed with water and distilled to give an 85% yield of pentanediol divinyl ether (b.p. 192° C.).

A 1 liter flask cooled to −12° C. was charged with 104 g pentanediol and a trace of methane sulfonic acid. To this solution was added 156 g pentanediol divinyl ether. The solution was stirred rapidly for 2 hours. Then slowly warmed to room temperature over a 6 hour period to give a viscous polymer having viscosity of 650 cst. at 100° F. (38° C.).

The product from the above reaction can be fluorinated in a liquid phase reactor containing 1,1,2-trichlorotrifluoroethane and a sufficient amount of fluorine to complex with all of the hydrogen fluoride formed during the reaction. A perfluoropolyether having the following structure is obtained:

$CF_3CF_2CF_2CF_2O (CF_2CF_2CF_2CF_2CF_2OCF(CF_3)O)_n$-$CF_2CF_2CF_2CF_3$.

EXAMPLE 9

A mixture of 400 g triethylene glycol ethyl ether (2.24 mol), 258 g acetaldehyde diethylacetal (1.39 mol), 300 ml benzene and 10 g acidic ion exchange resin were refluxed in a 1 liter stirred flask equipped with a continuous extractor to remove the by-product ethanol from the refluxing benzene. The solution was refluxed for 6 hours, then filtered and placed in a rotary evaporator to remove the benzene solvent.

The product was fluorinated in a 22 liter stirred tank which contained 5.7 liters of 1,1,2-trichlorotrifluoroethane and 1100 g sodium fluoride powder. The hydrocarbon, 219 g, was diluted to a volume of 700 ml with 1,1,2-trichlorotrifluoroethane. The solution was slowly pumped into the fluorination reactor, which was held at −5° C., over a period of 28 hours. The fluorine flow was set at a level approximately 10% higher than that required to react with all of the organic entering the reactor. Filtration of the crude reactor product followed by distillation yielded 224 g of a clear fluid which analyzed to be:

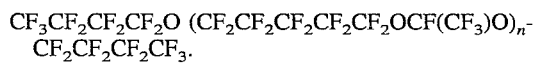

$CF_3CF_2OCF_2CF_2OCF_2CF_2OCF_2CF_2OCF(CF_3)OCF_2$-$CF_2OCF_2CF_2$ $^{19}F$ NMR (δppm vs $CFCl_3$):-86.5:$OCF(CF_3)$; −87.4:$CF_3CF_2O$; −88. O:$CF_2CF_2O$; −88.7:$OCF_2CF_2O$; −96.3:$OCF(CF_3)O$.

EXAMPLE 10

In an experiment very similar to the previous one, 400 g dipropylene glycol monomethylether (2.70 mol) was reacted with 159.5 g acetaldehyde diethylacetal (1.35 mol) in benzene with an acid catalyst. Fluorination of 250 g of the material afforded 480 g of a perfluorinated fluid having the following structure:

$CF_3OCF_2CF(CF_3)OCF_2CF(CF_3)OCF(CF_3)OCF_2CF$-$(CF_3)OCF_2CF(CF_3)OCF_3$.

EXAMPLE 11

Butoxyethoxyethanol (400 g, 2.47 mol) was reacted with 130 g polymeric chloroacetaldehyde in 150 ml benzene to give a fluid which distilled at 190° C. at approximately 1 torr. The product (266 g) was mixed with 500 ml 1,1,2-trichlorotrifluoroethane and pumped into a 15 liter fluorination reactor containing 5.7 liters 1,1,2-trichlorotrifluoroethane and 1,150 g sodium fluoride powder. Fluorine, diluted with approximately four volumes of nitrogen, was metered into the 0° C. reactor at a rate approximately 10% greater than that required to react stoichiometrically with the polyether. The organic feed rate was set to allow complete addition in approximately 23 hours. Filtration of the product and removal of the 1,1,2-trichlorotrifluoroethane via a distillation gave a fluorocarbon product which was further purified by a 12 hour fluorination at 200° C. with 40% fluorine. Approximately 520 g of fluid was recovered with approximately 50% being the target material.

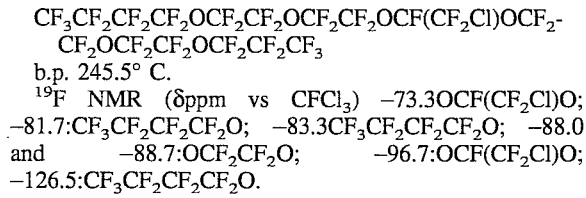

$CF_3CF_2CF_2CF_2OCF_2CF_2OCF_2CF_2OCF(CF_2Cl)OCF_2$-$CF_2OCF_2CF_2OCF_2CF_3$
b.p. 245.5° C.
$^{19}F$ NMR (δppm vs $CFCl_3$) −73.3$OCF(CF_2Cl)O$; −81.7:$CF_3CF_2CF_2CF_2O$; −83.3$CF_3CF_2CF_2CF_2O$; −88.0 and −88.7:$OCF_2CF_2O$; −96.7:$OCF(CF_2Cl)O$; −126.5:$CF_3CF_2CF_2CF_2O$.

EXAMPLE 12

Chloroacetaldehyde dimethyl acetal (124 g, 1 mol), 1,3-dichloro-2-propanol (258 g, 2 mol) and 5 g ion exchange resin were mixed in a 1 liter stirred flask. The mixture was heated to allow the methanol formed in the reaction to slowly distill from the flask. Approximately 70 ml of methanol was recovered over a 6 hour period. The remaining solution was vacuum-distilled and the fraction (120 g, 38% yield) boiling between 100 and 145° C. at 2 mm Hg was collected. The fluid was shown by $^{19}F$ NMR and elemental analysis to have the following structure:

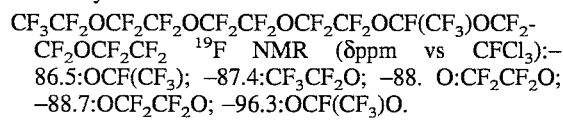

$(ClCH_2)_2CHOCHOCH(CH_2Cl)_2$
|
$CH_2Cl$

The above acetal (210 g) diluted with a small amount of chloroform and 1,1,2-trichlorotrifluoroethane was metered over a 14 hour period into a 22° C. fluorination reactor containing 5.7 liters of 1,1,2-trichlorotrifluoroethane. The crude product was further treated with 30% fluorine at 200° C. for several hours to give 197 g 157% yield) of clear fluid:

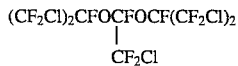

$(CF_2Cl)_2CFOCFOCF(CF_2Cl)_2$
|
$CF_2Cl$ b.p.: 202° C.
$^{19}F$ NMR (δppm vs $CFCl_3$):−64.5 and −65.0 (a), −71.0 (d), −86.7 (c) and −133.7 (b)

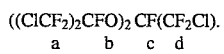

$((ClCF_2)_2CFO)_2 CF(CF_2Cl)$.
  a       b    c    d

EXAMPLE 13

Into a 1 liter stirred flask containing 300 ml benzene were placed 516 g 1,3-dichloro-2-propanol (4 mol), 120 g paraformaldehyde (4 mol) and 10 g ion exchange resin. The mixture was refluxed as the water formed during the reaction was continuously removed. After refluxing for 6 hours, the reaction mixture was filtered and vacuum distilled to give 354 g of a product with the following structure:

$(ClCH_2)_2CHOCH_2OCH(CH_2Cl)_2$
b.p.: 141° C./0.05 mm Hg.

The above acetal (354 g) was mixed with 70 g chloroform and 360 g 1,1,2-trichlorotrifluoroethane and fluorinated over a 24 hour period at 20° C. using the procedure described in the previous example. The reaction product was concentrated and the crude product was further treated with fluorine at 200° C. to give 430 g of a clear fluid (69% yield) having a boiling point of 178° C.

$^{19}F$ NMR (δppm vs $CFCl_3$):−45.5(c), −65.3(a) and −137.1(b)

$$((ClCF_2F)_2CFO)_2CF_2.$$
$$\phantom{((Cl}a\phantom{F_2F)_2}b\phantom{CF}c$$

EXAMPLE 14

A mixture of 300 g 1-propanol (5.0 mol), 231 g epichlorohydrin and 10 g ion exchange resin was refluxed for 22 hours. The reaction mixture was then cooled, filtered and distilled to give 281 g of 1-chloro-3propoxy-2-propanol (74% yield). Reaction of this product with paraformaldehyde (2.8 mol) gave 202 g of product (69% yield) having the following structure:

$$CH_3CH_2CH_2OCHOCH_2OCHCH_2OCH_2CH_2CH_3$$
$$\phantom{CH_3CH_2CH_2OC}|\phantom{HOCH_2OC}|$$
$$\phantom{CH_3CH_2CH_2O}CH_2Cl\phantom{OCH_2O}CH_2Cl$$

b.p.: 132° C. at 2 mm Hg.

Fluorination of the above acetal in a 23 hour reaction at 20° C. gave 404 g or product (81% yield) having the following structure:

$$CF_3CF_2CF_2OCF_2CFOCF_2OCFCF_2OCF_2CF_2CF_3$$
$$\phantom{CF_3CF_2CF_2OCF_2}|\phantom{FOCF_2O}|$$
$$\phantom{CF_3CF_2CF_2OCF_2}CF_2Cl\phantom{OC}CF_2Cl$$

b.p.: 207° C.

$^{19}$F NMR (δppm vs CFCl$_3$):–46.3(g), –67.3(f), –80.4(d) –81.9(a), –84.5(c), –130.0(b) and –141.6(e)

$$(CF_3CF_2CF_2OCF_2CF(CF_2Cl)O)_2CF_2.$$
$$\phantom{(}a\phantom{F_3}b\phantom{CF_2}c\phantom{CF_2}d\phantom{F(C}e\phantom{F_2Cl)}f\phantom{O)_2C}g$$

EXAMPLE 15

A mixture of 600 ml ethoxyethanol, 200 g epichlorohydrin and 10 g ion exchange resin was heated to 130° C. for 20 hours. The reaction mixture was then cooled, filtered and distilled to give 250 g of product which was then reacted with 116 g paraformaldehyde to give 266 g of a product boiling above 150° C. at 0.01 mm Hg.

Fluorination of 261 g of the product in a reactor containing 5 liters of 1,1,2-trichlorotrifluoroethane and 1000 g sodium fluoride gave 446 g of perfluorinated fluid of which approximately 70% had the following structure:

$$CF_3CF_2OCF_2CF_2OCF_2CFOCF_2OCFCF_2OCF_2CF_2OCF_2CF_3$$
$$\phantom{CF_3CF_2OCF_2CF_2OCF_2}|\phantom{FOCF_2OC}|$$
$$\phantom{CF_3CF_2OCF_2CF_2OCF_2}CF_2Cl\phantom{OC}CF_2Cl$$

b p. 224° C.

$^{19}$F NMR (δppm vs CFCl$_3$):–46.4(h), –67.6(g), –80.9(e), –87.6(a), –89.0(b,c,d), and –141.8(f)

$$CF_3CF_2OCF_2CF_2OCF_2CF(CF_2Cl)OCF_2OCF_2(CF_2Cl)CF_2OCF_2CF_2OCF_2CF_3.$$
$$a\phantom{F_3}b\phantom{CF_2O}c\phantom{CF_2}d\phantom{CF_2O}e\phantom{CF_2}f\phantom{(CF_2Cl)O}g\phantom{CF_2OC}h\phantom{CF_2O}f\phantom{(CF}g\phantom{CF_2Cl)}e\phantom{CF_2O}d\phantom{CF_2O}c\phantom{CF_2}b\phantom{CF_2O}a$$

EXAMPLE 16

A mixture consisting of 100 g 2-chloroethanol (12.4 mol), 573 g epichlorohydrin (6.2 mol) and 20 g of an acidic ion exchange resin were refluxed for 24 hours. The mixture was then filtered to remove the ion exchange resin and the excess alcohol and unreacted epichlorohydrin were removed by distillation. The residue was distilled under vacuum and the product 1-chloro-3-(2-chloroethoxy)2-propanol (804 g, 75% yield) distilled between 89 and 1° C. at 0.05 mm Hg.

Into a 1-liter stirred flask was placed 346 g 1-chloro-3-(2-chloroethoxy)-2-propanol (2 mol), 90 g paraformaldehyde (3 mol), 10 g ion exchange resin and 300 ml benzene. The mixture was refluxed for four hours as the water formed during the reaction was removed. The reaction mixture was filtered and distilled to give 267 g of a product (75% yield) with the following structure:

$$ClCH_2CH_2OCH_2CHOCH_2OCHCH_2OCH_2CH_2Cl$$
$$\phantom{ClCH_2CH_2OCH_2C}|\phantom{OCH_2OC}|$$
$$\phantom{ClCH_2CH_2OCH_2}CH_2Cl\phantom{OCH_2}CH_2Cl$$

Fluorination of the product (660 g) in a typical reaction at 20° C. gave 1086 g of a product (82% yield) having the following structure:

$$ClCF_2CF_2OCF_2CFOCF_2OCFCF_2OCF_2CF_2Cl$$
$$\phantom{ClCF_2CF_2OCF_2}|\phantom{FOCF_2OC}|$$
$$\phantom{ClCF_2CF_2OCF_2}CF_2Cl\phantom{OC}CF_2Cl$$

b.p.: 223° C.

$^{19}$F NMR: (δppm vs CFC$_{l3}$):–46.3(f), –67.3(e), –74.3(a), –81.0(c), –87.3(b) and –141.9(d)

$$(ClCF_2CF_2OCF_2CF(CF_2Cl)O)_2CF_2.$$
$$\phantom{(Cl}a\phantom{F_2}b\phantom{CF_2O}c\phantom{CF_2}d\phantom{F(C}e\phantom{F_2Cl)O)_2}f$$

EXAMPLE 17

Into a 1 liter flask was charged 300 g trichloropentaerythritol, (1.58 mol), 150 ml of benzene, 10 g ion exchange resin and 60 g paraformaldehyde (2 mol). The mixture was refluxed as water was being removed continuously.

A portion of the above product, 192 g, was diluted with 1,1,2-trichlorotrifluoroethane to give 210 ml of solution which was pumped into a 22° C. reactor containing 4.3 liters of 1,1,2-trichlorotrifluoroethane. The reaction was complete in approximately 8 hours. The unreacted fluorine was flushed from the reactor with nitrogen gas and the product (307 g, 87.8% yield) was recovered by distillation:

$^{19}$F NMR (δppm vs CFCl$_3$): –48.9(a), –51.1(c), –66.4(b)

$$((ClCF_2)_3CCF_2O)CF_2.$$
$$\phantom{((Cl}a\phantom{F_2)_3C}b\phantom{CF_2O)}c$$

Equivalents

Those skilled in the art will recognize or be able to ascertain using no more than routine experimentation many equivalents to the specific embodiments of the invention described herein. Such equivalents are intended to be encompassed by the following claims.

We claim:

1. A perfluorinated gem-alkylenedioxy composition which is normally liquid and consists essentially of one or a mixture of perfluorinated gem-alkylenedioxy compounds having at least 12 carbon atoms.

2. A perfluoroacetal composition which consists essentially of one or more saturated perfluoro-1,1-bis-(alkoxy) alkane compounds each of which compounds can have two perfluoro-1,1-alkylenedioxy moieties provided such moieties are separated from each other by at least two catenary carbon atoms of a perfluoroalkylene moiety.

3. The composition of claim 1 consisting essentially of one of said compounds.

4. The composition of claim 1 consisting essentially of a mixture of said compounds.

5. The composition of claim 1 wherein said compound is represented by the formula $CF_3CF_2CF_2CF_2OCF_2CF_2OCF_2CF_2OCF_2OCF_2$ $CF_2OCF_2 CF_2OCF_2CF_2CF_2CF_3$.

6. The composition of claim 1 wherein said compound is represented by the formula $CF_3CF_2OCF_2CF_2OCF_2CF_2OCF_2CF_2OCF_2CF_2O\text{-}CF_2CF_2OCF_2CF_2OCF_2CF_3$.

7. The composition of claim 1 wherein said compound is represented by the formula $CF_3CF_2CF_2CF_2OCF_2CF_2OCF_2CF_2OCF_2CF_2OCF_2OC\text{-}F_2CF_2OCF_2CF_2OCF_2CF_2OCF_2CF_2CF_3$.

8. The composition of claim 1 wherein said compound is represented by the formula $CF_3CF_2CF_2CF_2OCF_2CF_2OCF_2CF_2OCF_2CF_2OCF_2CF_2\text{-}OCF_2OCF_2CF_2OCF_2CF_2OCF_2CF_2OCF_2CF_2OCF_2C\text{-}F_2CF_2CF_3$.

9. The composition of claim 1 wherein said compound is represented by the formula $CF_3CF_2O(CF_2CF_2O)_3CF(CF_3)O$ $(CF_2CF_2)_2CF(CF_3)O(CF_2CF_2O)_3CF_2CF_3$.

10. The composition of claim 1 wherein said compound is represented by the formula $CF_3CF_2OCF_2CF_2OCF_2CF_2OCF_2CF_2OCF_2$ $(CF_3)OCF_2CF_2OCF_2CF_2OCF_3CF_3$.

11. The composition of claim 1 wherein said compound is represented by the formula $CF_3CF_2CF_2CF_2OCF_2CF_2OCF_2CF_2OCF$ $(CF_2Cl)OCF_2CF_2OCF_2CF_2OCF_2CF_2CF_3$.

12. The composition of claim 1 wherein said compound is represented by the formula $CF_3CF_2CF_2OCF_2CF(CF_2Cl)OCF_2OCF(CF_2Cl)$ $CF_2OCF_2CF_2CF_3$.

13. The composition of claim 1 wherein said compound is represented by the formula $CF_3CF_2OCF_2CF_2OCF_2CF(CF_2Cl)$  $OCF_2OCF(CF_2Cl)$ $CF_2OCF_2CF_2OCF_2CF_3$.

14. The composition of claim 1 wherein said compound is represented by the formula $CF_3O(CF(CF_3)CF_2O)_3CF_2(OCF(CF_3)CF_2)_3OCF_3$.

15. The composition of claim 1 wherein said compound is represented by the formula $CF_3CF_2O(CF_2CF_2O)_3CF(CF_3)O(CF_2CF_2O)_2CF(CF_3)O\text{-}(CF_2CF_2O)_3CF_2CF_3$.

16. The composition of claim 1 wherein said compound is represented by the formula $CF_3OCF_2CF(CF_3)OCF_2CF(CF_3)OCF(CF_3)OCF_2CF\text{-}(CF_3)OCF_2CF(CF_3)OCF_3$.

17. $CF_3OC_3F_6OC_3F_6OCF_2OC_3F_6OC_3F_6OCF_3$.

18. $(ClCF_2)_2CFOCF(CF_2Cl)OCF(CF_2Cl)_2$.

19. $(ClCF_2)_2CFOCF_2OCF(CF_2Cl)_2$.

20. $ClCF_2CF_2OCF_2CF(CF_2Cl)OCF_2OCF(CF_2Cl)CF_2OCF_2\text{-}CF_2Cl$.

* * * * *